(12) United States Patent
Cha et al.

(10) Patent No.: US 10,893,916 B2
(45) Date of Patent: Jan. 19, 2021

(54) END EFFECTOR HAVING LINE LASER MOUNTED THEREIN

(71) Applicant: CUREXO, INC., Seoul (KR)

(72) Inventors: Yong Yeob Cha, Ulsan (KR); Heung Soon Lim, Ulsan (KR); Dong Gi Woo, Ulsan (KR); Han Cheol Choi, Ulsan (KR); Hong Ho Kim, Ulsan (KR)

(73) Assignee: CUREXO, INC., Seoul (KR)

( * ) Notice: Subject to any disclaimer, the term of this patent is extended or adjusted under 35 U.S.C. 154(b) by 110 days.

(21) Appl. No.: 16/312,485

(22) PCT Filed: Jun. 20, 2017

(86) PCT No.: PCT/KR2017/006457
§ 371 (c)(1),
(2) Date: Dec. 21, 2018

(87) PCT Pub. No.: WO2017/222274
PCT Pub. Date: Dec. 28, 2017

(65) Prior Publication Data
US 2019/0142543 A1    May 16, 2019

(30) Foreign Application Priority Data

Jun. 21, 2016  (KR) .................... 10-2016-0077615

(51) Int. Cl.
*A61B 90/13*   (2016.01)
*A61B 6/03*    (2006.01)
(Continued)

(52) U.S. Cl.
CPC ............. *A61B 90/13* (2016.02); *A61B 6/03* (2013.01); *A61B 6/032* (2013.01); *A61B 10/02* (2013.01);
(Continued)

(58) Field of Classification Search
CPC ........... A61B 90/00; A61B 6/03; A61B 10/02; A61B 6/032; A61B 10/0233; A61B 17/3403; A61B 90/13; A61B 17/3409
See application file for complete search history.

(56) References Cited

U.S. PATENT DOCUMENTS

| 5,957,933 A | 9/1999 | Yanof et al. |
| 2010/0106056 A1 | 4/2010 | Norris et al. |
| 2010/0323320 A1 | 12/2010 | Takebayashi |

FOREIGN PATENT DOCUMENTS

| KR | 10-2014-0056772 A | 5/2014 |
| KR | 10-2015-0000232 A | 1/2015 |
| WO | 2014-185746 A1 | 11/2014 |

*Primary Examiner* — George J Ulsh
(74) *Attorney, Agent, or Firm* — Novick, Kim & Lee, PLLC; Jae Youn Kim; Jihun Kim

(57) ABSTRACT

The present invention relates to an end effector having a line laser mounted therein, comprising: a main body forming the body of an end effector; a support part installed in the main body and supporting needle guide apparatuses for guiding a needle; a line laser part installed on one side and the other side of the support part, and emitting line laser beams so as to mark a needle insertion point for inserting the needle into a lesion of a patient; and a guide part for guiding the line laser beams emitted from the line laser part so as to cross the line laser beams, wherein the line laser part emits the line laser beams via the guide part such that the needle insertion point is marked at a predetermined distance away from the needle guide apparatus.

7 Claims, 7 Drawing Sheets

(51) Int. Cl.
*A61B 10/02* (2006.01)
*A61B 17/34* (2006.01)
(52) U.S. Cl.
CPC ...... *A61B 10/0233* (2013.01); *A61B 17/3403* (2013.01); *A61B 2017/3409* (2013.01)

END EFFECTOR HAVING LINE LASER MOUNTED THEREIN

TECHNICAL FIELD

The present invention relates to an end effector equipped with a line laser for an interventional procedure of inserting a needle into a lesion of a patient with image information such as CT (Computerized Tomography) for biopsy and treatment.

BACKGROUND ART

In general, interventional procedure is performed by inserting a medical apparatus into body while observing the inside of human body with an imaging device and means medical technology used over all for both internal and surgical procedures such as biopsy, dilatation, drug injection, and so on.

There is an intervention procedure of needle-insertion type using a needle as a medical tool. The intervention procedure of needle-insertion type is performed by inserting the needle into an inside of human body and used not only in the area of tissue biopsy for chest, abdomen and various organ lesion, and high frequency, alcohol, freezing, radiation local treatment at lesion part, but also in approach method of lesion when various stent and tube are installed. It is used in most interventional procedures The intervention procedure of needle-insertion type is performed for inspection or treatment by inserting the medical needle directly to a desired inspection site or desired treatment lesion through skin with looking at images acquired by an imaging device used in radiology such as CT (Computerized Tomography), MRI (Magnetic Resonance Imager).

As disclosed in Republic of Korea Patent Publication No. 10-2014-0056772 (Oct. 13, 2012), a method where an operator manipulates an operation part of a robot for the intervention procedure of needle-insertion type is applied recently.

An end effector, a needle insertion apparatus, is attached to such an intervention procedure robot, and the needle is installed at the distal end of the end effector before the intervention procedure.

Conventionally, a marking device made of metal material such as a laser could not be installed in the end effector for the radiolucency through a needle insertion apparatus part of the end effector. Accordingly, there are problems that an operator has to predict a position of a needle insertion site before the procedure and perform anesthesia or incision, and it could not be easily visually checked whether the needle is inserted correctly into the incision region during the procedure.

DETAILED DESCRIPTION OF THE INVENTION

Technical Problem

The present invention is to solve the problems as described and provide an end effector equipped with a line laser which is capable of marking a needle insertion point and keeps the radiolucency even if the end effector is tilted within a certain angle.

Solution to Problem

In order to achieve the above object, an end effector equipped with a line laser according to an aspect of the present invention comprises: a main body being the body of the end effector; a support part installed in the main body and supporting a needle guide apparatus for guiding a needle; a line laser part installed on one side and the other side of the support part and emitting line laser beams so as to mark a needle insertion point on a lesion of patient where the needle is inserted; and a guide part for guiding the line laser beam so as to cross the line laser beams irradiated from the line laser part, wherein the line laser part irradiates the line laser beams via the guide part such that the needle insertion point is marked at a predetermine distance away from the needle guide apparatus.

Herein, the line laser part may comprises a first line laser apparatus installed on the one side and a second line laser apparatus installed on the other side of the support part, and the guide part may be formed through the main body, and comprise a first guide hole which the line laser beam from the first line laser apparatus passes through and a second guide whole which is formed apart from the first guide hole and the line laser beam from the second line laser apparatus passes through, wherein the first guide hole and the second guide hole are formed in the main body such that a spaced distance between the first and second guide holes decreases in a forward direction from the support part to the needle guide apparatus and thus the line laser beams irradiated by the first line laser apparatus and the second line laser apparatus respectively are crossed.

In addition, the first line laser apparatus and the second line laser apparatus are coupled with the support part to be symmetrical about the needle guide apparatus and the first line laser apparatus may be coupled with the support part to be movable in a first direction from the one side to the other side of the support part and the second line laser apparatus may be coupled with the support part to be movable in a second direction opposite to the first direction.

Also, the first line laser apparatus and the second line laser apparatus may be coupled with the support part to be movable in at least one of the forward direction or a top side direction opposite to a bottom side direction which the line laser beam is irradiated.

Preferably, in the end effector equipped with the line laser the line laser part may be installed in the support part not to interfere with CT (Computerized Tomography), an imaging device's photographing a tip of the needle from top side to bottom side direction of the end effector.

Also, the needle insertion point may be a first cross point where the line laser beams irradiated by the first laser apparatus and the second line laser apparatus are crossed first below the needle guide apparatus.

Advantageous Effects of Invention

According to the present invention, no artifact in photographing CT is caused by metal material even if the end effector is tilted within a certain angle, and the needle insertion point can be marked so that the operator can perform anesthesia or incision conveniently.

MODE FOR THE INVENTION

In this specification, it is noted that the same reference numbers are used to denote the same elements even if they are shown in the other drawings.

Meanwhile, the meaning of terms described in the present invention should be understood as follows.

The singular expressions are to be understood as including plural expressions unless the context defines obviously differently, and the terms like "the first", "the second" are used to distinguish one element from other element so that the scope of the right should not be limited by these terms.

It should be understood that the terms like "comprise" or "have" do not preclude of one or more other features, numbers, steps, movements, elements, components, or the presence of combinations thereof or additional possibility.

It should be understood that the term of "at least one" comprises all possible combinations that can be presented from one or more related items. For example, "at least one of the first item, the second item and the third item" means combinations of all items that can be provided by two or more of the first item, the second item and the third item as well as each of the first item, the second item or the third item.

Hereinafter, an end effector equipped with a line laser according to the present invention will be described in detail with reference to attached drawings.

Figure 1:
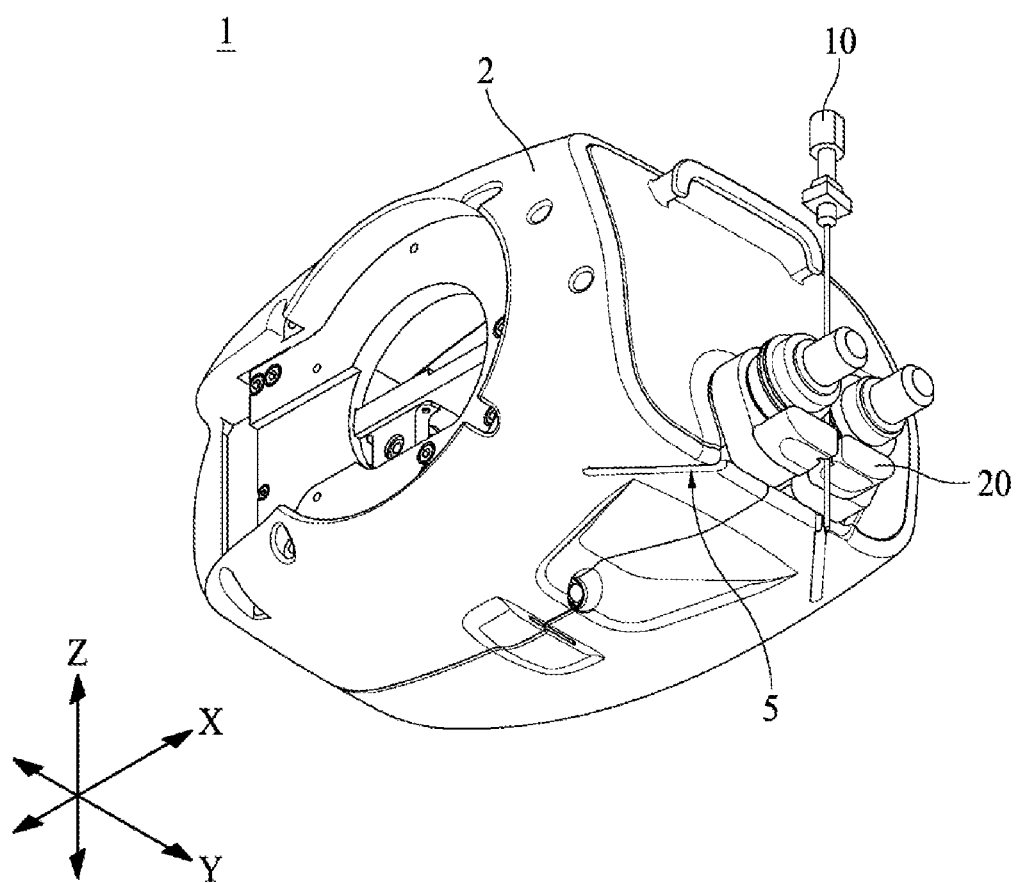
FIG. 1 is a schematic perspective view of an end effector equipped with a line laser according to the present invention.
Figure 2:
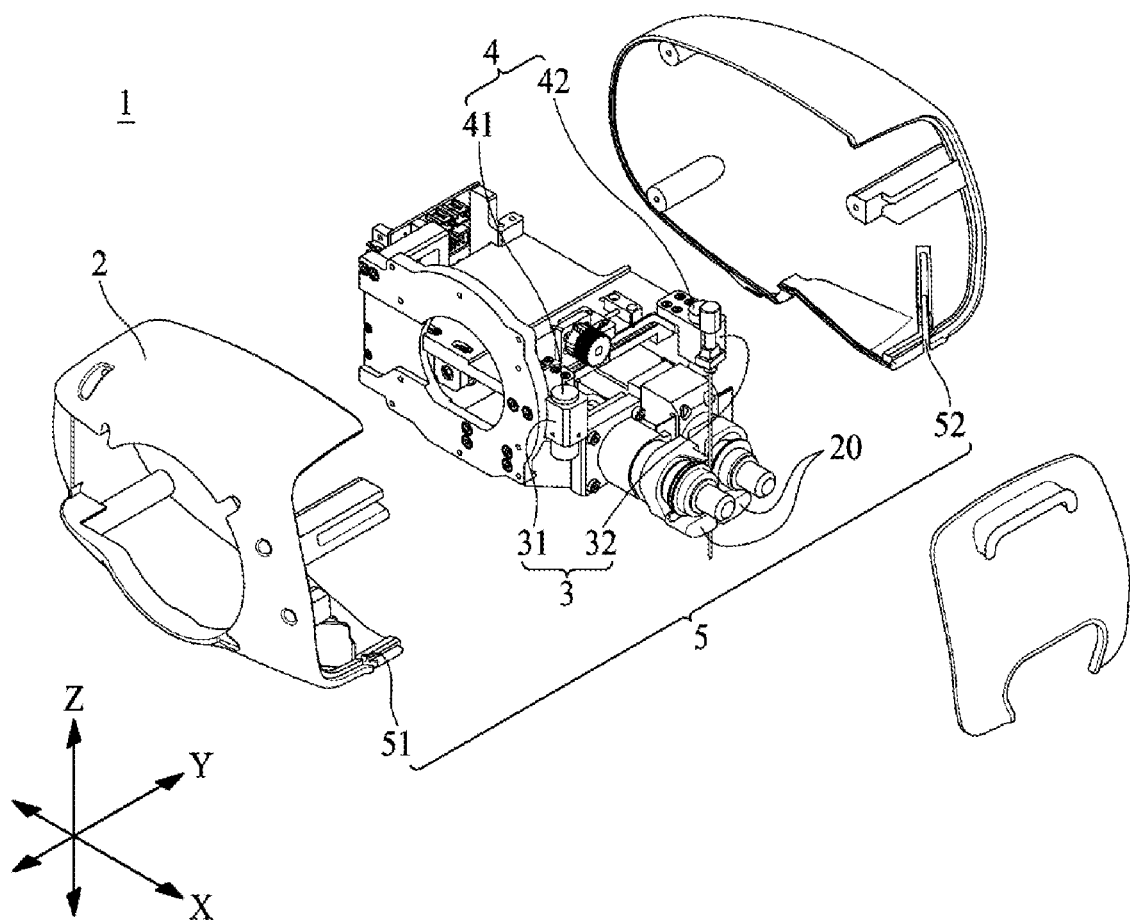
FIG. 2 is a schematic disassembled perspective view of an end effector equipped with a line laser according to the present invention.
Figure 3:
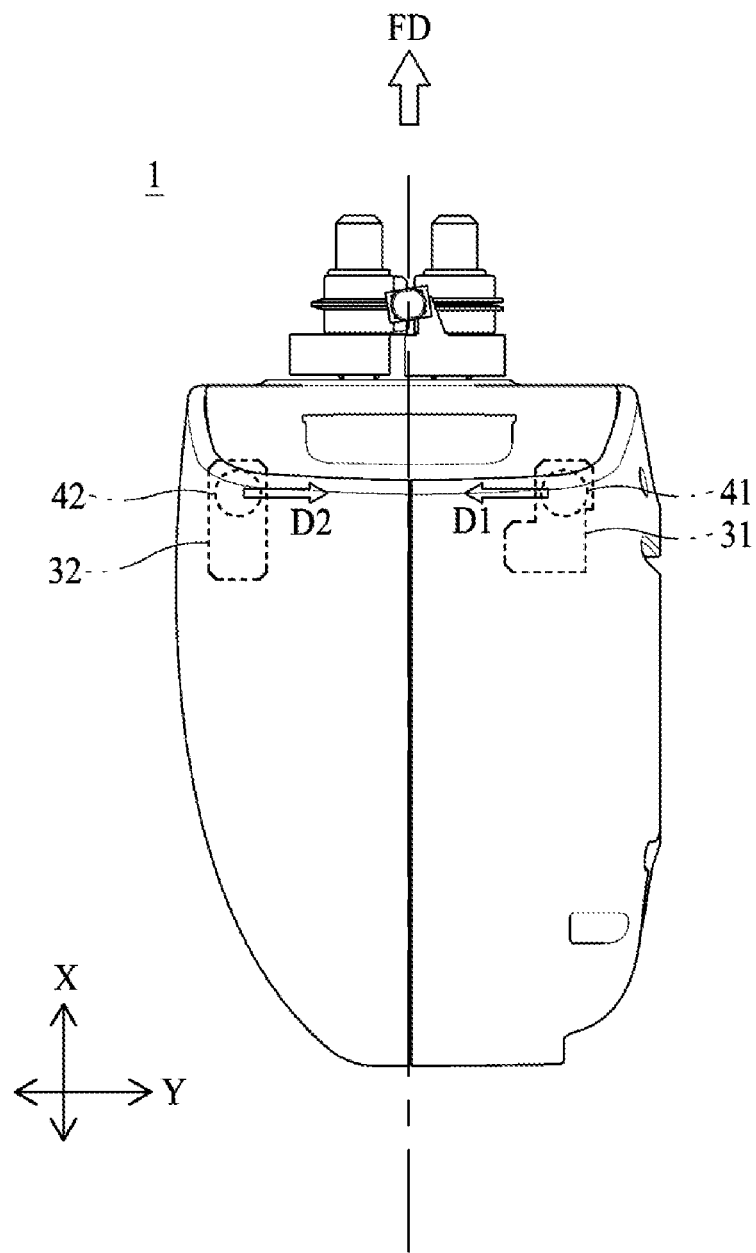
FIG. 3 is a schematic plan view for explaining a line laser part of an end effector according to the present invention.
Figure 4:
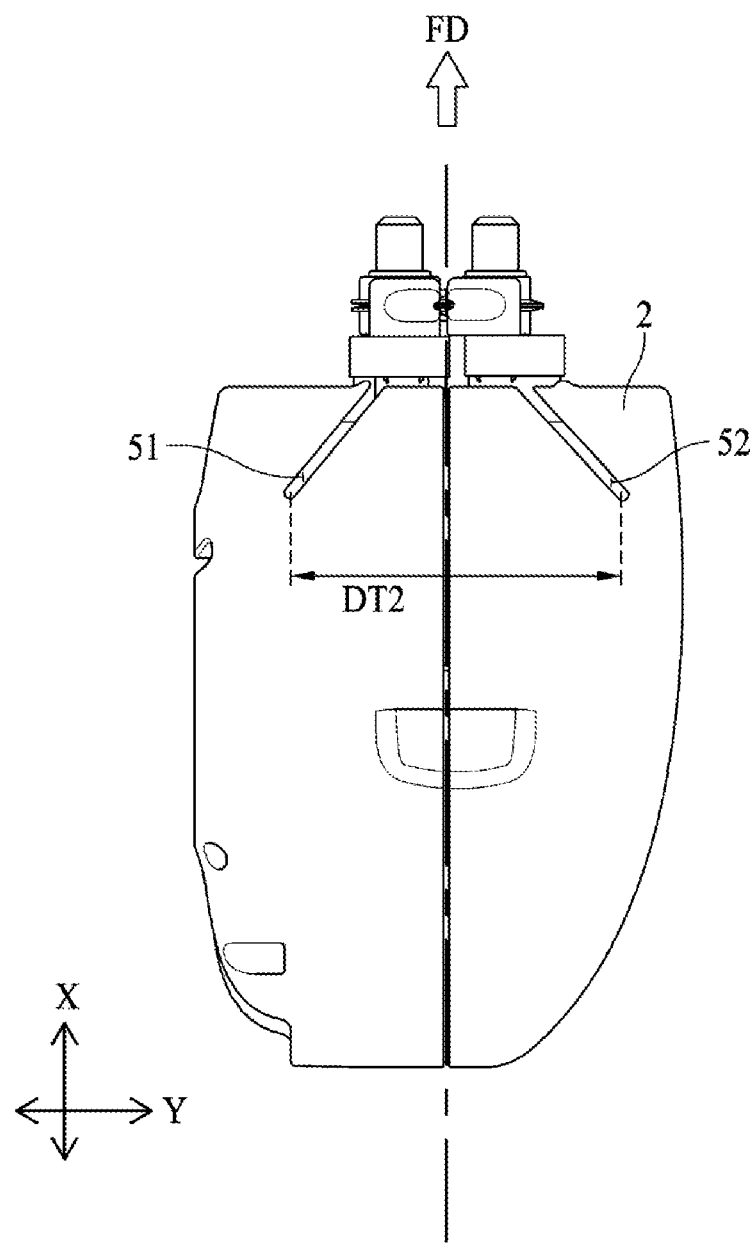
FIG. 4 is a schematic bottom view for explaining a guide part of an end effector equipped with a line laser according to the present invention.
Figure 5:
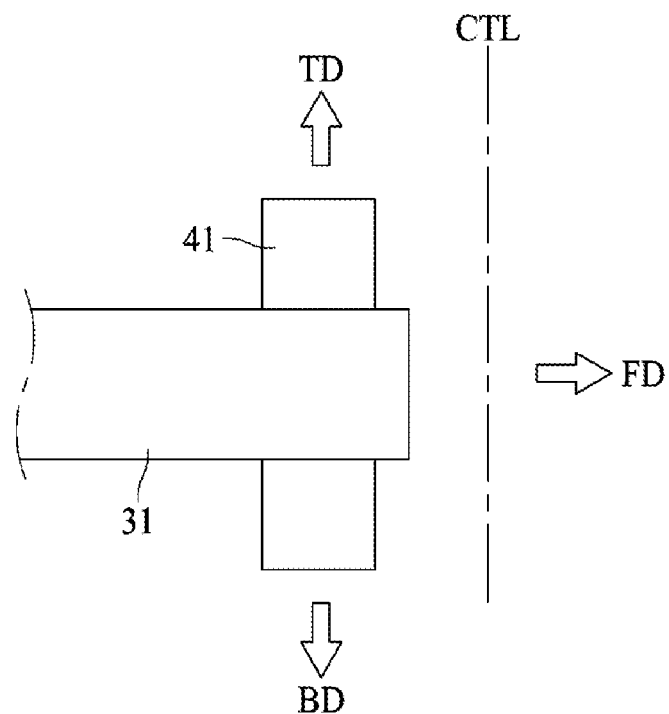
FIG. 5 to FIG. 7 are schematic operation state view for explaining that a line laser part according to the present invention does not interfere with a computer tomography even if the end effector equipped with the line laser is tilted within a certain angle.
Figure 6:
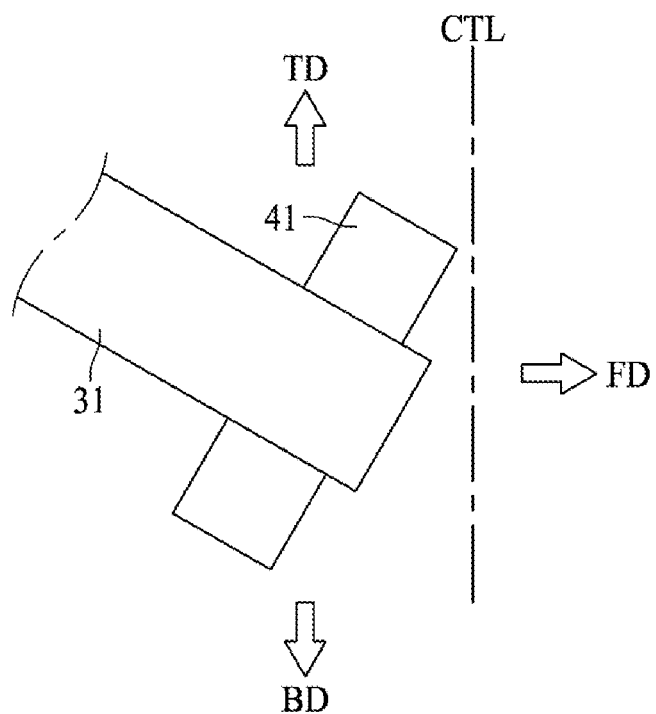
Figure 7:
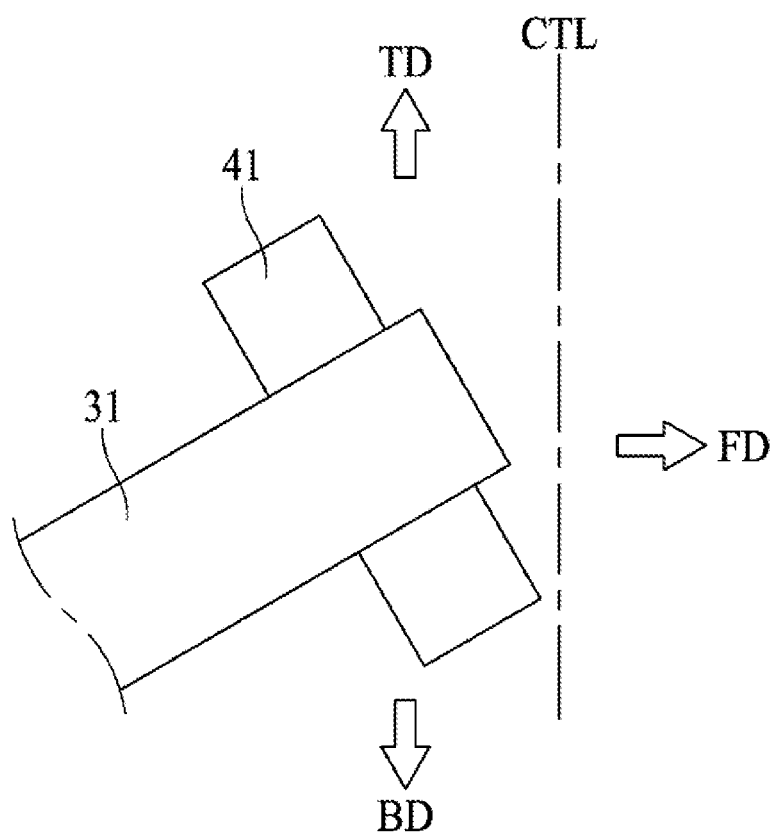
Figure 8:
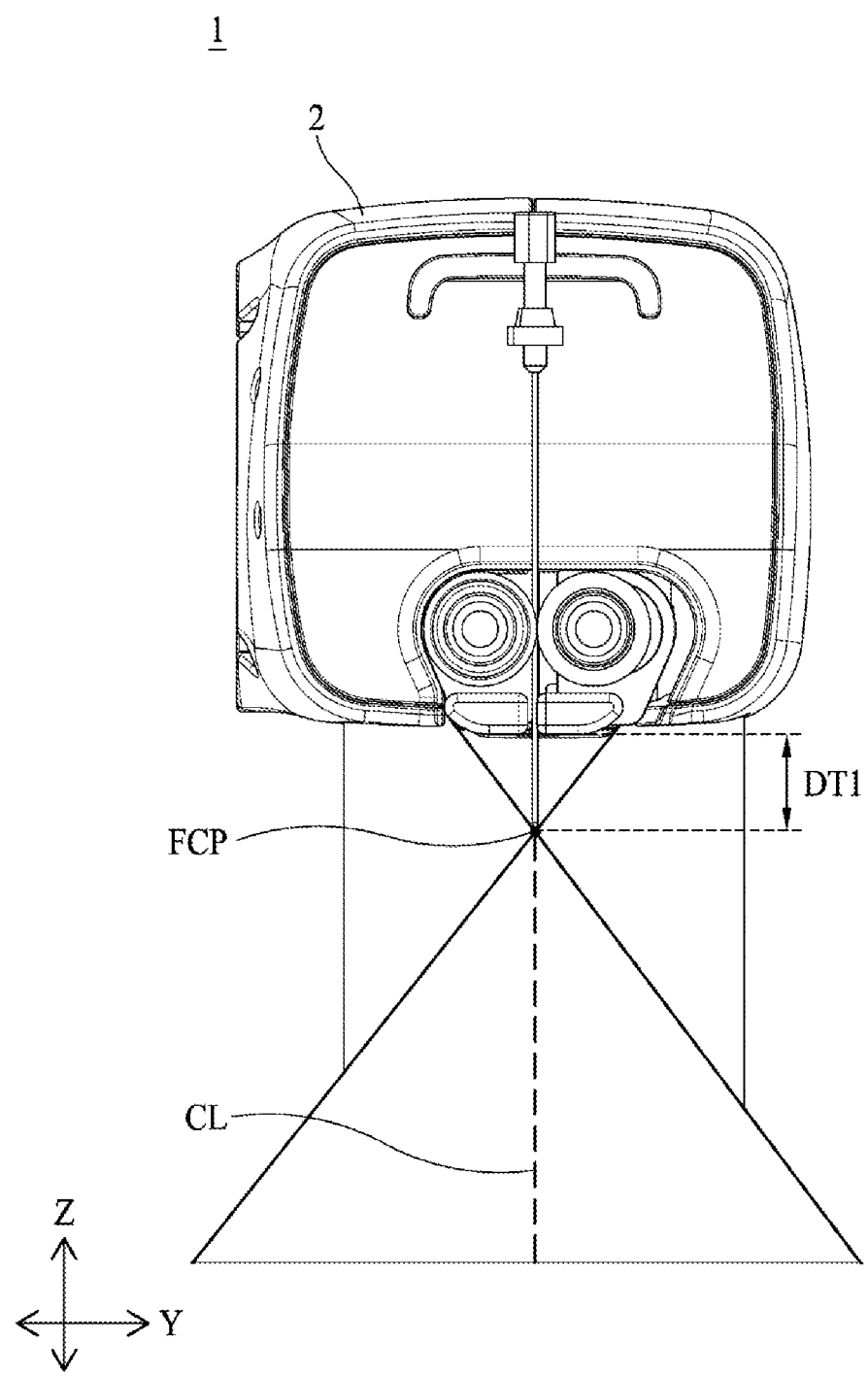
FIG. 8 is a schematic front view for explaining that an end effector equipped with a line laser according to the present invention marks a needle insertion point

FIG. 1 is a schematic perspective view of an end effector equipped with a line laser according to the present invention, FIG. 2 is a schematic disassembled perspective view of the end effector equipped with the line laser according to the present invention, FIG. 3 is a schematic plan view for explaining the line laser part of the end effector according to the present invention, FIG. 4 is a schematic bottom view for explaining a guide part of the end effector equipped with the line laser according to the present invention, FIG. 5 to FIG. 7 are schematic operation state view for explaining that the line laser part according to the present invention doesn't interfere with a computer tomography even if the end effector equipped with the line laser is tilted within a certain angle and FIG. 8 is a schematic front view for explaining that the end effector equipped with the line laser according to the present invention marks a needle insertion point Referring to FIG. 1 to FIG. 8, the end effector 1 equipped with the line laser according to the present invention is for marking a needle insertion point with line laser beam where an interventional procedure needle is inserted on a lesion of patient. Particularly, the end effector 1 equipped with the line laser according to the present invention can mark the needle insertion point without interference with the computerized tomography (CT) even if it is tilted in a certain angle.

For this, the end effector 1 equipped with the line laser according to the present invention mainly comprises a main body 2, a support part 3, a line laser part 4, a guide part 5.

The end effector 1 equipped with the line laser according to the present can be coupled with a robot composed of multiple joints. The end effector 1 holds an interventional procedure needle (hereinafter referred to as 'needle') and inserts the needle into lesion of patient where the needle insertion point is marked. An imaging device for computed tomography such as CT (Computerized Tomography) can be installed in the forward direction of the end effector 1 (FD, shown in FIG. 5). Although not shown, the CT acquires images of the tip of the needle 10 in the view from the top side direction (TD, shown in FIG. 5) to the bottom side direction (BD, shown in FIG. 5). The CT photographing line (CTL, shown in FIG. 5) may be orthogonal to the lesion of the patient which the present invention is not limited to.

Hereinafter, the main body 2, the support part 3, the line laser part 4, and the guide part 5 will be described in detail with reference to the attached drawings.

Referring to FIG. 1 to FIG. 8, the main body 2 forms the body of the end effector 1. The main body 2 encloses the support part 3, the line laser part 4, and a driving part for holding and inserting the needle 10 inside. The main body 2 may block the impurities such as dust, etc. not to penetrate into the support part 3, the line laser part 4 and the driving part. The main body 2 may be formed of a hollow hexahedron overall. But it is not limited thereto, and it may be formed in another shape if the support part 3, the line laser part 4, and driving part. etc may be installed inside it.

A needle guide apparatus 20 for supporting the needle 10 may be protruded outside the main body 2. The needle guide apparatus 20 may be coupled to the support part 3 such that the needle guide apparatus 20 is positioned at a front end of the main body 2 along the X-axis (shown in FIG. 1). The needle guide apparatus 20 may be positioned at a center between one side and the other side of the main body 2 in the front end of the main body 2. Herein, one side of the main body 2 means the right side of the main body 2 about the needle guide apparatus 20. The other side of the main body 2 means the left side of the main body 2 about the needle guide apparatus 20. That is, one side and the other side of the main body 2 are respectively positioned in direction of Y-axis (shown in FIG. 1) perpendicular to the X-axis, and may be symmetrical with the X-axis. The needle guide apparatus 20 may guide a needle 10 at the central front end of the main body 2.

The main body 2 may be coupled with the multiple-joint robot. The main body 2 may be moved as the joint of multiple-joint robot moves. Accordingly, the main body 2 may be inclined so that the needle guide apparatus 20 is positioned lower than the bottom side of the main body 2. Herein, the top side and bottom side mean the upward direction and downward direction along the Z-axis (shown in FIG. 1). For example, assuming that horizontal state where the main body 2 is not inclined is 0°, the main body 2 may be inclined to +10° from the horizontal state. In this case, the end of the needle 10 may be inclined in a direction toward inside of the main body 2. The main body 2 may be inclined so that the needle guide apparatus 20 is positioned higher than the bottom side of the main body 2. For example, the end of the needle 10 may be inclined to −10° from the horizontal state. In this case, the end of the needle 10 may be inclined in a direction toward outside of the main body 2. The main body 2 may be positioned in the horizontal state so that the needle guide apparatus 20 is not inclined. In this case, the needle 10 may be positioned perpendicular to the horizontal plane without tilting. In this case, the needle 10 may be overlapped in the CT photographing line (CTL, shown in FIG. 5).

The support part 3 is installed inside of the main body 2. The support part 3 has rectangular planar shape roughly and is coupled with the main body 2 by a method such as interference fit, screw connection, or adhesive bonding. The needle guide apparatus 20 to guide a needle 10 is coupled with the support part 3. Accordingly, the support part 3 based on the main body 2 supports the needle guide apparatus 20. Also, a driving part (not shown) for inserting the line laser part 4 and the needle 10 may be coupled with the support part 3. The first line laser apparatus 41 and the second line laser apparatus 42 of the line laser part 4 may be movably coupled with one side 31 and the other side 32 of the support part 3 respectively. The one side 31 of the support part 3 may be positioned on the right side of the main body 2. The other side 32 of the support part 3 may be positioned on the left side of the main body 2. Therefore, the needle guide apparatus 20 may be positioned between the one side 31 and the other side 32 of the support part 3. For example, the needle guide apparatus 20 may be coupled so to be positioned at central point between the one side 31 and the other side 32 of the support part 3. Also, the needle guide apparatus 20 may be coupled with the support part 3 so as to protrude from the front end of the main body 2. Accordingly, the needle guide apparatus 20 may guide the needle 10 at the front end of the end effector 1.

The line laser part 4 irradiates a line laser beam to mark a needle insertion point where a needle 10 is inserted into a lesion of patient. The line laser part 4 may irradiate the line laser beam toward a bottom direction (BD, shown in FIG. 5) as the lesion of patient is positioned below the end effector 1. The line laser part 4 may be installed in the support part 4 not to interfere with CT photographing a tip of the needle in bottom direction (BD) in a state where the CT is installed in forward direction (FD) of the end effector 1. On the interference of the CT photographing, the lesion of patient and the tip of the needle do not photograph accurately well due to the line laser part 4 of a metal material. The line laser part 4 may be installed in the support part 3 so as not to interfere with the CT photographing line (CTL) even if the end effector 1 is tilted to ±10° by multiple joints robot.

The line laser part 4 may comprise a first line laser apparatus 41 and the second line laser apparatus 42 installed respectively on the one side 31 and the other side 32 of the support part 3. The first line laser apparatus 41 and the second line laser apparatus 42 may be coupled with one side 31 and the other side 32 of the support part to be symmetric about the needle guide apparatus 20. Accordingly, the first line laser apparatus 41 and the second line laser apparatus 42 may be positioned in the same line on the Y-axis. Therefore, the line laser beam from the first line laser apparatus 41 and the line laser beam from the second line laser apparatus 42 may be respectively irradiated from the positions where are spaced each other on the same line.

The first line laser apparatus 41 may be coupled with the support part 3 to be movable in a first direction (D1, shown in FIG. 3) from the one side 31 of the support part 3 to the other side 32 of the support part 3. The second line laser apparatus 42 may be coupled with the support part 3 to be movable in a second direction (D2, shown in FIG. 3) opposite to the first direction D1. The first line laser apparatus 41 cannot be moved in the second direction D2. This is because the size of the end effector 1 is increased. For the same reason, the second line laser apparatus 42 cannot be moved in the first direction (D1). The first line laser apparatus 41 may be moved in the second direction D2 after being moved in the first direction D1 and the second line laser 42 may be moved in the first direction D1 after being moved in the second direction D2. For example, the first line laser apparatus 41 can be moved in less than 0.5 mm in the first direction D1. The first line laser apparatus 41 cannot be moved in more than 0.5 mm because the driving part is installed there. The second line laser apparatus 42 can be moved in less than 0.8 mm in the second direction D2. The second line laser apparatus 42 cannot be moved in more than 0.8 mm because the driving part is installed there. When the first line laser apparatus 41 is moved in the first direction D1 and the second line laser apparatus 42 is moved in the second direction D2, a distance (DT2, shown in FIG. 4) where the first line laser apparatus 41 and the second line laser apparatus 42 are spaced apart may be decreased. In this case, a crossing point of the line laser beams irradiated through the guide part 5 is formed lower than that of the case where the first line laser apparatus 41 and the second line laser apparatus 42 are not moved. That is, the needle insertion point may be formed lower. Accordingly, the end effector 1 equipped with the line laser according to the present invention can easily adjust the distance (DT1, shown in FIG. 8) spaced between the needle guide apparatus 20 and the needle insertion point as the first line laser apparatus 41 and the second line laser apparatus 42 are installed movably. The first line laser apparatus 41 and the second line laser apparatus 42 may be moved in the support part 3 with means of cylinder type using hydraulic cylinder or a pneumatic cylinder, a gear type using a motor, a rack gear, a pinion gear, a ball screw type using a motor and a ball screw, a belt type using a motor, a pulley and a belt, or a linear motor type using a coil and a permanent magnet. The first line laser apparatus 41 and the second line laser apparatus 42 may be moved by an operator.

The first line laser apparatus 41 and the line laser apparatus 42 may be coupled with the support part 3 so as to be movable in at least one direction of forward direction (FD, shown in FIG. 3) and top side direction TD opposite to the bottom side direction BD where the line laser beams are irradiated. Since moving the first line laser apparatus 41 and the second line laser apparatus 42 to forward direction FD and top side direction TD are similar, moving them in any one direction will be explained herein.

The first line laser apparatus 41 may be moved in forward direction FD. For example, the first line laser apparatus 41 may be moved in less than 4.8 mm in forward direction FD. Because if the first line laser apparatus 41 moves in more than 4.8 mm, it may interfere with the CT photographing line CTL.

As the first line laser apparatus 41 is moved in the forward direction FD, the range of the line laser beam irradiated through the guide part 5 may be narrowed in the inside direction of the main body 2. The first line laser apparatus 41 cannot move in backward direction opposite to forward direction FD due to components installed inside the main body 2. Therefore, the first line laser apparatus 41 may be moved in the backward direction when it is moved in the forward direction FD.

The first line laser apparatus 41 may be moved in top side direction TD. For example, the first line laser apparatus 41 may be moved in less than 3.6 mm in top side direction TD. When the first line laser apparatus 41 moves in more than 3.6 mm, the needle insertion point may not be marked because the line laser beam interferes with the driving part installed inside the main body 2 and is not irradiated to outside of the main body 2. As the first line laser apparatus 41 moves in a top side direction TD, the line laser beam irradiated through the guide part 5 may be narrowed in the inside direction of the main body 2. In the end effector 1 equipped with the line laser according to the present invention, when the irradiation range of the line laser beam is narrowed as described above, the needle insertion point may be marked lower than that before moving the first line laser apparatus 41. Therefore, the end effector 1 equipped with the line laser according to the present invention may easily adjust the marking position of the needle insertion point by moving the line laser part 4 in at least one direction among the first direction D1, the second direction D2, the forward direction FD or the top side direction TD.

The guide part 5 may guide the line laser beams to cross the line laser beams irradiated from the line laser part 4. The guide part 5 is formed through the bottom side of the main body 2 so that the line laser beams from the line laser part 4 installed inside of the main body 2 are irradiated in the bottom side direction BD of the main body 2. The guide part 5 may guide the line laser beams differently according to the shape through the main body 2. The guide part 5 may comprise a first guide hole 51 and a second guide hole 52.

The first guide hole 51 may be formed through the main body 2 to be positioned below the one side 31 of the support part 3 where the first line laser apparatus 41 is installed. Accordingly, the line laser beam from the first line laser apparatus 41 may be irradiated in the bottom side direction BD through the first guide hole 51. The line laser beam from the first line laser apparatus 41 interferes with the main body 2 so that it cannot be irradiated to the outside of the main body 2 except for the first guide hole 51. The first guide hole 51 may be formed in a planar cross shape of '|' passing through the main body 2 so that the line laser beam below the main body 2 may be irradiated in the plane shape. Accordingly, the line laser beam below the main body 2 may be irradiated so that the irradiation range is gradually widened in the shape of '|'. As the first line laser apparatus 41 moves to the first direction D1, the forward direction FD and the top side direction TD in the state where the first guide hole 51 is fixed, the line laser beam irradiated outside the main body 2 may be moved. In this case, the cross point where it crosses with the line laser beam from the second line laser apparatus 42 may be formed at a position different from that before moving.

The second guide hole 52 may be formed at a position spaced apart from the first guide hole 51. The second guide hole 52 may be formed through the main body 2 to be positioned below the other side 32 of the support part 3 where the second line laser apparatus 42 is installed. Accordingly, the line laser beam from the second line laser apparatus 42 may be irradiated in the bottom side direction BD through the second guide hole 52. The line laser beam from the second line laser apparatus 42 interferes with the main body 2 so that it cannot be irradiated to the outside of the main body 2 except for the second guide hole 52. The second guide hole 52 may be formed in a planar cross shape of '|' passing through the main body 2 so that the line laser beam below the main body 2 may be irradiated in the planar shape. Accordingly, the line laser beam below the main body 2 may be irradiated so that the irradiation range is gradually widened in the shape of '|'. As the second line laser apparatus 42 moves to the second direction D2, the forward direction FD and the top side direction TD in the state where the second guide hole 52 is fixed, the line laser beam irradiated outside the main body 2 may be moved. In this case, the cross point where it crosses with the line laser beam from the first line laser apparatus 41 may be formed at a position different from that before moving.

The first guide hole 51 and the second guide hole 52 may be formed in the main body 2 so that the more it moves in the forward direction FD, the more the spaced distance DT2 is decreased. Accordingly, the line laser beams irradiated respectively by the first line laser apparatus 51 and the second line laser apparatus 52 may be crossed each other. For example, in view from a top side direction (TD) to a bottom side direction (BD), the first guide hole 51 may be formed in the main body 2 in the planar sectional shape of '\', the second guide hole 52 may be formed in the main body 2 in the planar sectional shape of '/'. Accordingly, the line laser beams irradiated respectively by the first line laser apparatus 51 and the second line laser apparatus 52 may be crossed in the shape of 'Λ' of 'X' below the needle guide apparatus 20. If the first guide hole 51 is form in the planar sectional shape of '|' and the second guide hole 52 is form in the planar sectional shape of '|', the line laser beams irradiated respectively by the first line laser apparatus 51 and the second line laser apparatus 52 cannot be crossed each other. In addition, even if the first guide hole 51 is form in the planar sectional shape of '/' and the second guide hole 52 is form in the planar sectional shape of '\ ', the line laser beams irradiated respectively by the first line laser apparatus 51 and the second line laser apparatus 52 cannot be crossed. Therefore, the end effector 1 equipped with the line laser according to the present invention can cross the line laser beams below the needle guide apparatus 20 to mark the needle insertion point by forming the first guide hole 51 in the shape of '\' and the second guide hole 52 in the shape of '/'.

The needle insertion point may be the first crossing point (FCP, shown in FIG. 8) where the line laser beams irradiated respectively by the first line laser apparatus 51 and the second line laser apparatus 52 are crossed below the needle guide apparatus 20. In this case, the needle insertion point may be marked at a predetermine distance DT1 away from the needle guide apparatus 20. For example, the distance may be 21 mm and may be preset by the operator. Although not shown, the line laser beams irradiated respectively by the first line laser apparatus 51 and the second line laser apparatus 52 are not crossed within a predetermine distance, and thus the needle insertion point is not marked. When the predetermine distance is exceeded, the line laser beams irradiated respectively by the first line laser apparatus 51 and the second line laser apparatus 52 are crossed in a shape of 'X'. Therefore, in the end effector 1 equipped with the line laser according to the present invention position, the line laser part 4 and the guide part 5 are arranged such that the needle insertion point is formed in the position farther than that of the predetermined distance away from the needle guide apparatus 20, and thus the operator not only performs anesthesia or incision conveniently, but also increases the probability of success of an interventional procedure and improves the patient's satisfaction. The needle 10 inserted into the needle insertion point may be inserted deeply into a lesion of patient along the crossing line (CL, shown in FIG. 8) where the line laser beams are crossed.

The present invention described above is not limited to the above-described embodiment and the accompanying drawings, but it will be apparent to those skilled in the art that various modifications, substitutions and alterations will be possible without departing from the technical idea of the invention.

What is claimed is:

1. An end effector equipped with a line laser, the end effector comprising:
   a main body;
   a needle guide apparatus for guiding a needle and positioned at a front end of the main body;

a support part accommodated in the main body and supporting the needle guide apparatus;

a line laser emitter accommodated in the main body and configured to emit a first line laser beam and a second line laser beam so as to mark a needle insertion point on a lesion of patient where the needle is inserted; and a guide part positioned on a bottom side of the main body to guide the first line laser beam and the second line laser beam from the line laser emitter in the main body so as for the first and the second line laser beams to cross each other, wherein the line laser emitter includes a first line laser apparatus disposed on one side of the support part and configured to emit the first line laser beam, and a second line laser apparatus disposed on another side of the support part and configured to emit the second line laser beam, and wherein the first line laser apparatus and the second line laser apparatus are movably disposed on the support part such that the needle insertion point is marked at an adjustable distance away from the needle guide apparatus.

2. The end effector according to claim 1, wherein the guide part comprises a first guide hole which the first line laser beam from the first line laser apparatus passes through and a second guide hole which is located apart from the first guide hole and the second line laser beam from the second line laser apparatus passes through, and the first guide hole and the second guide hole are formed in the bottom side of the main body such that a spaced distance between the first and second guide holes decreases in a forward direction from the support part to the needle guide apparatus and the first line laser beam and the second line laser beam cross each other at a point that is lower than the needle guide apparatus.

3. The end effector according to claim 2, wherein the first line laser apparatus and the second line laser apparatus are coupled with the support part to be movable in at least one of the forward direction or a top side direction opposite to a bottom side direction in which the first and the second line laser beams are irradiated; and the distance between the needle insertion point and the needle guide apparatus is adjusted according to a movement of at least one of the first line laser apparatus and the second line laser apparatus.

4. The end effector according to claim 1, wherein the first line laser apparatus and the second line laser apparatus are coupled with the support part to be symmetrical about the needle guide apparatus.

5. The end effector according to claim 1, wherein the first line laser apparatus is coupled with the support part to be movable in a first direction from one side to another side of the support part, the second line laser apparatus is coupled with the support part to be movable in a second direction opposite to the first direction, and the distance between the needle insertion point and the needle guide apparatus is adjusted according to a movement of at least one of the first line laser apparatus and the second line laser apparatus.

6. The end effector according to claim 1, wherein the line laser emitter disposed on the support part is configured not to interfere with a CT (Computerized Tomography) imaging line, even when the main body is inclined within a predetermined angle with respect to the CT imaging line, and wherein the effector is configured such that a tip of the needle is photographed by a CT device in a direction from a top side to a bottom side of the end effector.

7. The end effector according to claim 1, wherein the needle insertion point is a first cross point where the first line laser beam and the second line laser beam irradiated by the first laser apparatus and the second line laser apparatus are crossed first below the needle guide apparatus.

\* \* \* \* \*